United States Patent [19]
Lashinski et al.

[11] Patent Number: 6,129,738
[45] Date of Patent: Oct. 10, 2000

[54] METHOD AND APPARATUS FOR TREATING STENOSES AT BIFURCATED REGIONS

[75] Inventors: Randall T. Lashinski; Philip J. Haarstad; Matthew J. Birdsall, all of Santa Rosa, Calif.

[73] Assignee: Medtronic AVE, Inc., Santa Rosa, Calif.

[21] Appl. No.: 09/100,416

[22] Filed: Jun. 20, 1998

[51] Int. Cl.$^7$ .................................................. A61M 29/00
[52] U.S. Cl. .................... 606/194; 604/101.04; 623/1.35
[58] Field of Search .................................. 606/191, 194, 606/195, 198; 623/1, 1.11, 1.35; 604/96–101, 101.01, 101.04, 101.05, 103.04

[56] References Cited

U.S. PATENT DOCUMENTS

| | | |
|---|---|---|
| 4,580,568 | 4/1986 | Gianturco . |
| 4,733,665 | 3/1988 | Palmaz . |
| 4,739,762 | 4/1988 | Palmaz . |
| 4,776,337 | 10/1988 | Palmaz . |
| 4,830,003 | 5/1989 | Wolff . |
| 4,913,141 | 4/1990 | Hillstead . |
| 4,969,458 | 11/1990 | Wiktor . |
| 4,994,071 | 2/1991 | MacGregor . |
| 5,019,090 | 5/1991 | Pinchuk . |
| 5,292,331 | 3/1994 | Boneau . |
| 5,320,605 | 6/1994 | Sahota ..................... 604/101 |
| 5,613,946 | 3/1997 | McKeever ................. 604/101 |
| 5,667,521 | 9/1997 | Keown ..................... 606/194 |
| 5,669,924 | 9/1997 | Shaknovich . |
| 5,718,683 | 2/1998 | Reesemann et al. .................... 606/194 |
| 5,718,724 | 2/1998 | Goicoechea et al. . |
| 5,720,735 | 2/1998 | Dorros . |
| 5,723,004 | 3/1998 | Dereume . |
| 5,749,825 | 5/1998 | Fischell et al. . |
| 5,749,848 | 5/1998 | Jang et al. . |
| 5,749,888 | 5/1998 | Yock . |
| 5,755,735 | 5/1998 | Richter et al. . |
| 5,755,771 | 5/1998 | Penn et al. . |

FOREIGN PATENT DOCUMENTS 0 804 907 A2   5/1997   European Pat. Off. .

OTHER PUBLICATIONS

Foley et al., "Bifurcation Lesion Stenting", The Thoraxcentre Journal, vol. 8, No. 4, Dec. 1996.
Freed, M.D. et al., "The New Manual of Interventional Cardiology", Chapter 10, pp. 238–243, 1996.

Primary Examiner—Michael Buiz
Assistant Examiner—William Lewis

[57] ABSTRACT

A method and apparatus for treating stenoses at bifurcated regions of body lumens is disclosed. A balloon catheter system is disclosed comprising two balloon catheters, or a balloon catheter having a bifurcated distal end, with a linking guide wire lumen at the distal end of one balloon catheter, or one branch of the bifurcated catheter, for linking the two balloons or branches such that the device can be tracked to a treatment site. Once at the treatment site, the balloon catheters or branches of the bifurcated distal end can be unlinked and separately positioned within the branches of the bifurcated body lumen. The apparatus can also serve as a delivery system for multiple prostheses or a bifurcated endoluminal prosthesis.

24 Claims, 20 Drawing Sheets

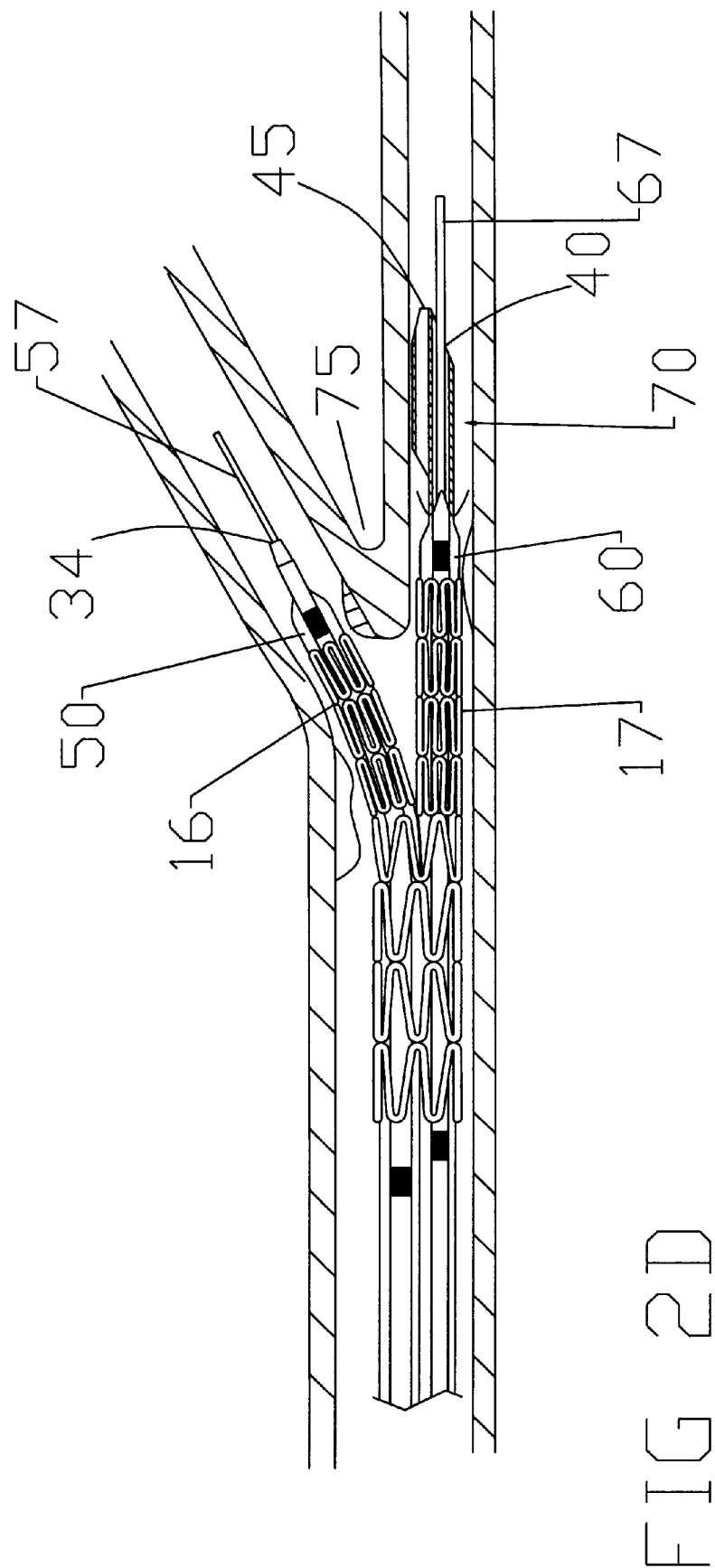

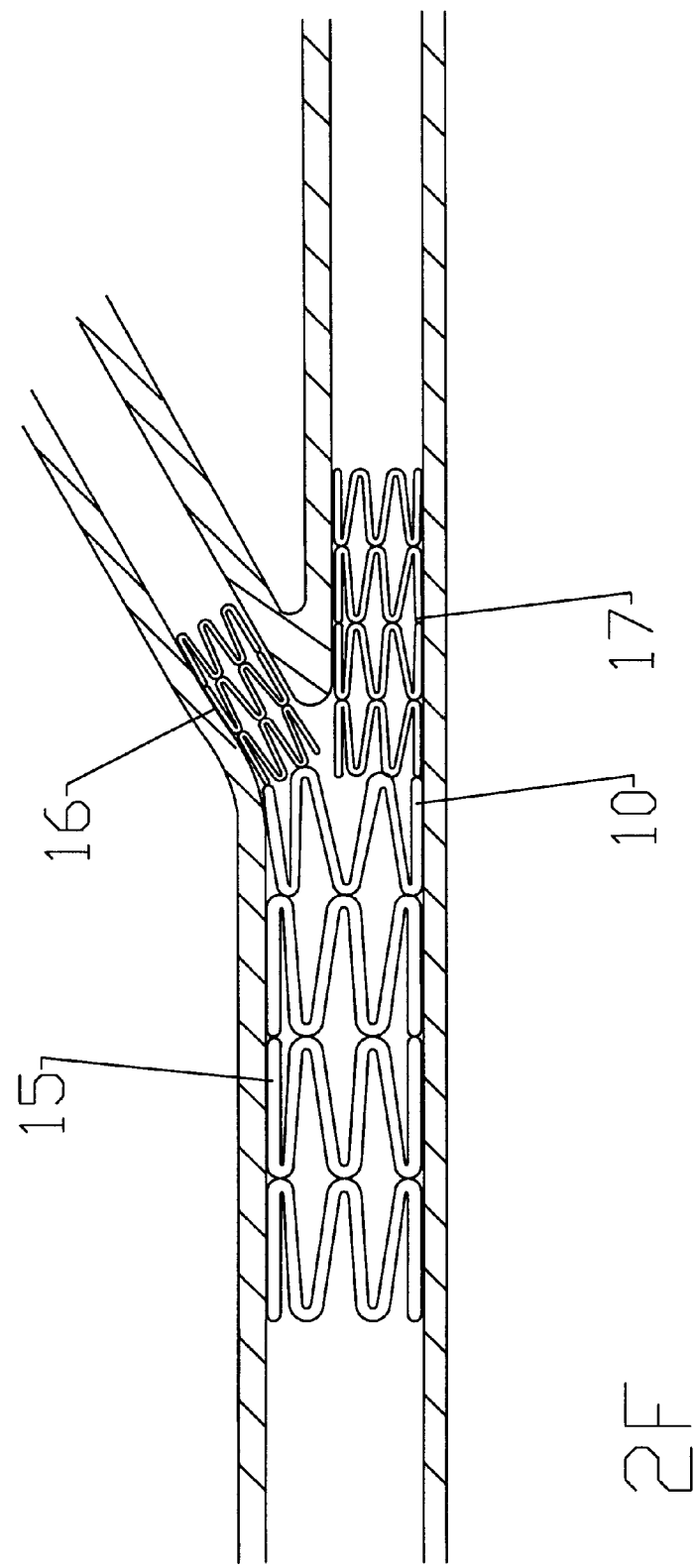

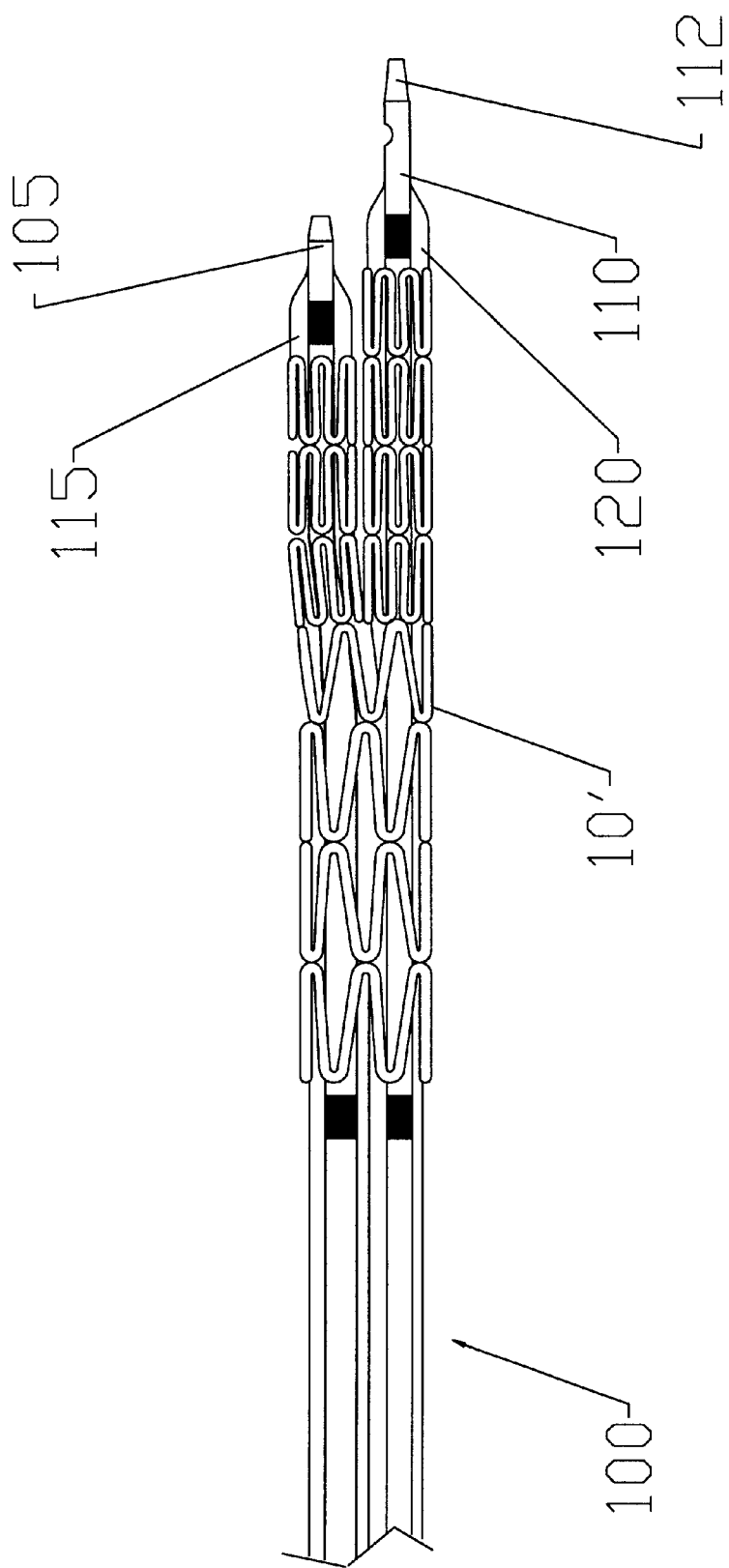

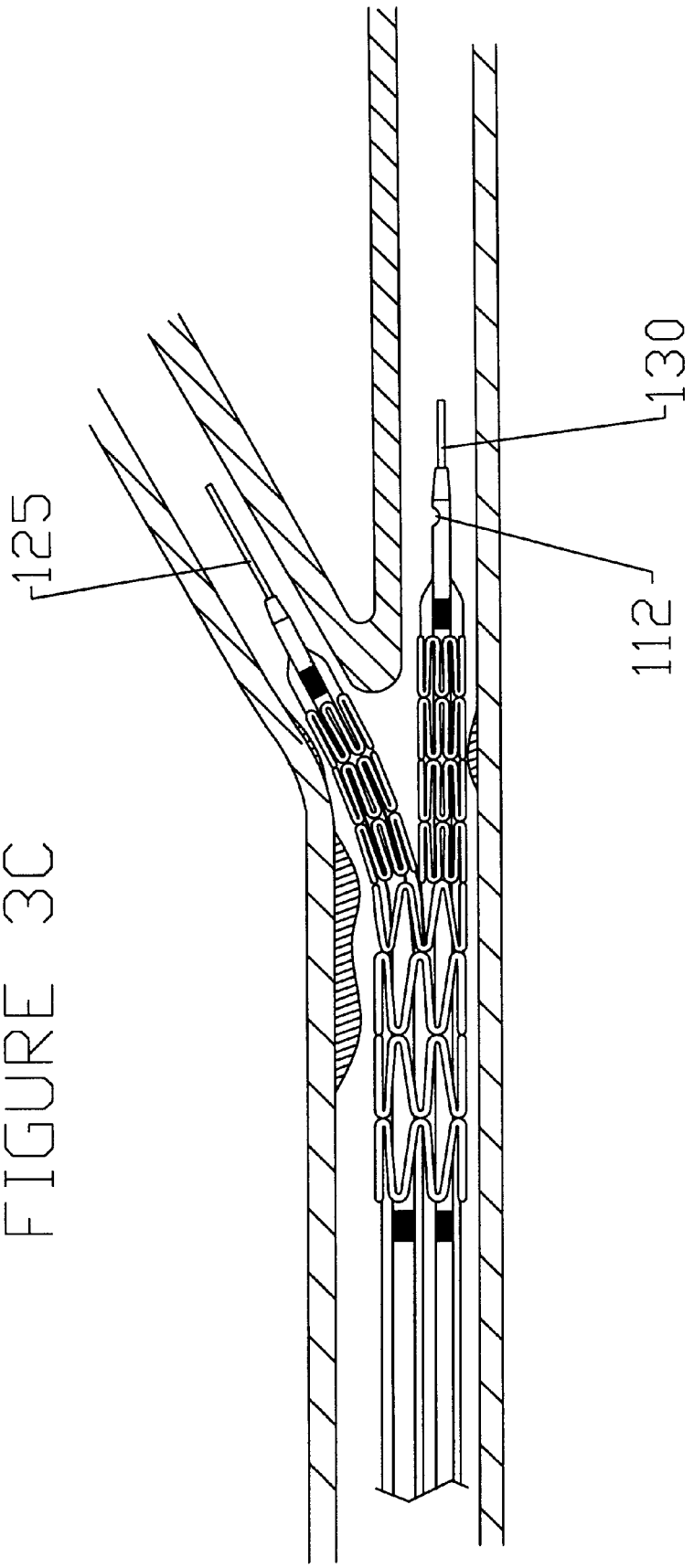

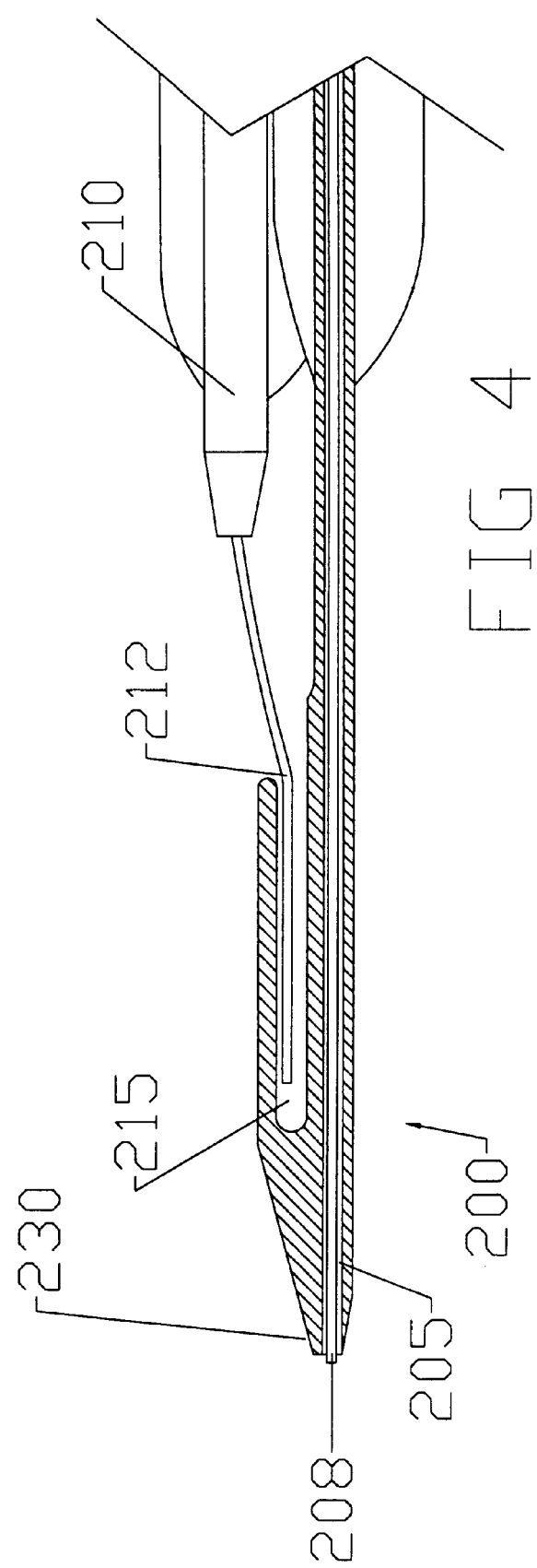

METHOD AND APPARATUS FOR TREATING STENOSES AT BIFURCATED REGIONS

FIELD OF THE INVENTION

This invention relates to dilatation catheters, stents and grafts for dilating strictures or stenoses in the human body. More particularly, the invention relates to a balloon catheter, including a delivery system for a bifurcated endoluminal prosthesis, for treating site or sites at or near a bifurcation of a body lumen.

BACKGROUND OF THE INVENTION

The use of balloon catheters with or without stents to treat strictures, stenoses, or narrowings in various parts of the human body is well known in the prior art. Devices of numerous designs have been utilized for angioplasty, stents and grafts or combination stent/grafts. And varied catheter designs have been developed for the dilatation of stenoses and to deliver prostheses to treatment sites within the body lumen.

Devices developed specifically to address the problems that arise in the treatment of stenoses at or near the site of a bifurcation of a body lumen are known in the art. Examples of catheters for use in treating bifurcated lumens or delivery systems for bifurcated endoluminal prostheses are shown in U.S. Pat. No. 5,720,735 to Dorros, U.S. Pat. No. 5,669,924 to Shaknovich, U.S. Pat. No. 5,749,825 to Fischell, et al., and U.S. Pat. No. 5,718,724 to Goicoechea et al.

Various techniques have been used to deliver multiple prostheses in order to provide radial support to both a main blood vessel, for example, and contemporaneously to side branches of the blood vessel. Further, single bifurcated stents and grafts have been developed in order to treat such conditions at the site of a branch of a body lumen. A bifurcated stent and/or graft typically comprises a tubular body or trunk and two tubular legs. Examples of bifurcated stents are shown in U.S. Pat. No. 5,723,004 to Dereume et al., U.S. Pat. No. 4,994,071 to MacGregor, and European Pat. Application EP 0 804 907 A2 to Richter, et al.

Illustrative procedures involving balloon catheters include percutaneous transluminal angioplasty (PTA) and percutaneous transluminal coronary angioplasty (PTCA), which may be used to reduce arterial build-up such as caused by the accumulation of atherosclerotic plaque. These procedures involve passing a balloon catheter over a guide wire to a stenosis with the aid of a guide catheter. The guide wire extends from a remote incision to the site of the stenosis, and typically across the lesion. The balloon catheter is passed over the guide wire, and ultimately positioned across the lesion.

Once the balloon catheter is positioned appropriately across the lesion, (e.g., under fluoroscopic guidance), the balloon is inflated, which breaks the plaque of the stenosis and causes the arterial cross section to increase. Then the balloon is deflated and withdrawn over the guide wire into the guide catheter, and from the body of the patient.

In many cases, a stent or other prosthesis must be implanted to provide permanent support for the artery. When such a device is to be implanted, a balloon catheter which carries a stent on its balloon is deployed at the site of the stenosis. The balloon and accompanying prosthesis are positioned at the location of the stenosis, and the balloon is inflated to circumferentially expand and thereby implant the prosthesis. Thereafter, the balloon is deflated and the catheter and the guide wire are withdrawn from the patient.

Administering PTCA and/or implanting a stent at a bifurcation in a body lumen poses further challenges for the effective treatment of stenoses in the lumen. For example, dilating a vessel at a bifurcation may cause narrowing of an adjacent branch of the vessel. In response to such a challenge, attempts to simultaneously dilate both branches of the bifurcated vessel have been pursued. These attempts include deploying more than one balloon, more than one prosthesis, a bifurcated prosthesis, or some combination of the foregoing.

However, simultaneously deploying multiple and/or bifurcated balloons with or without endoluminal prostheses, hereinafter individually and collectively referred to as a bifurcated assembly, requires highly accurate placement of the assembly. Specifically, deploying a bifurcated assembly requires positioning a main body of the assembly within the trunk of the vessel adjacent the bifurcation, and then positioning the independent legs of the assembly into separately branching legs of the body lumen.

Tracking a bifurcated assembly to a treatment site also presents additional challenges to the more standard PTCA procedure. For example, a bifurcated catheter must be tracked to the site as a unitary device until it reaches the bifurcation. Once it reaches the bifurcated treatment site, it must be positioned within the separate branches of the vessel. Therefore, it must be a unitary device during tracking and be a bifurcated device for treatment.

In order to achieve the foregoing objectives, objectives, two guide wires are typically required, one for placement of the assembly into each branch of the bifurcated vessel. Devices known in the prior art fail to track and position a device requiring two guide wires in an expeditious fashion by failing to prevent the entanglement of the wires or other complications which would prevent proper placement of the assembly and/or a smooth withdrawal the catheter and of the guide wires.

Further, devices known in the prior art fail to provide a bifurcated assembly, the distal portion of which functions as a unitary device during tracking and as a bifurcated device for positioning and deployment.

In view of the foregoing, it is an object of this invention to provide improved catheters and methods for use with multiple guide wires for delivering balloon catheters and prostheses designed to treat stenoses at or near a bifurcation of a body lumen.

SUMMARY OF THE INVENTION

These and other objects of the invention are accomplished in accordance with the principles of the invention by providing catheters which can be linked together, with which multiple guide wires can be utilized and which will prevent the entanglement of the multiple guide wires. These objects are further accomplished by providing a catheter with a structure which allows the distal ends of two catheters or the bifurcated distal end of a bifurcated catheter to function initially as one unit tracked over a single guidewire and then subsequently as two separate members, in order to be accurately positioned within a bifurcation of a body lumen. While the preferred embodiments set forth herein incorporate a single catheter with a bifurcated distal end, it is understood that the descriptions of the invention apply to separate catheters as well. The present invention can be utilized with catheters which are rapid-exchange, over the wire, a combination of the two, or other design.

A catheter according to the present invention comprises a distal tip structure attached to one portion of the distal end of the assembly. The distal tip structure houses a linking guide wire lumen.

In a typical use of catheters constructed in accordance with this invention, a first guide wire is already in place in the body lumen, with a proximal end protruding from the body. A second guide wire is threaded through the catheter through a guide wire lumen, referred to as the second guide wire lumen. Alternatively, with some embodiments, the second guide wire may be threaded through the catheter at a later point. The second guide wire lumen is also housed within the distal tip structure. The second guide wire may or may not extend through the distal tip of the catheter.

In order to introduce the catheter into the body lumen, the distal tip of the catheter is threaded onto the proximal end of the first guide wire. The first guide wire is threaded through the linking guide wire lumen housed within the distal tip structure connected to one portion, and into a first guide wire lumen located in the adjacent portion, such that it links the otherwise unconnected or bifurcated distal tip of the catheter or catheters. The temporarily unified distal end of the assembly is then passed over the first guide wire to the site of the bifurcation of the body lumen.

With the aid of fluoroscopy, the assembly is positioned appropriately near the site of the bifurcation, with the distal tip structure extending into a branch of the body lumen. The first guide wire is then withdrawn from the linking guide wire lumen, and consequently from the distal tip structure, freeing the branches of the bifurcated assembly from one another, and allowing the independent positioning of the catheter portions via their respective guide wires.

The second guide wire remains within the second guide wire lumen. The first guide wire now extends only through the first guide wire lumen. The first guide wire and consequently the first balloon can then tracked into a side branch of the body lumen. The second guide wire and second balloon is tracked into the adjacent vessel branch. The main body of the assembly remains in the trunk of the vessel. The bifurcated or first and second balloons can then be inflated. If a prosthesis is mounted upon the assembly, the first and second balloons circumferentially expand the main body and the first and second legs of the bifurcated prosthesis.

Following the dilation of the body lumen, and after the prosthesis, if any, has been implanted, the balloons are deflated. Preferably both guide wires remain in the patient during the withdrawal of the catheter or catheters. However, one guide wire may be withdrawn from the patient, and then the catheter may be withdrawn from the patient along the remaining guide wire. Assuming that there is no further need for a guide wire following the withdrawal of the catheter or catheters, the guide wires may also be withdrawn.

Further features of the invention, its nature and various advantages, will be more apparent from the accompanying drawings and the following detailed description of the preferred embodiments.

BRIEF DESCRIPTION OF THE DRAWINGS

FIG. 1A illustrates the catheter in vivo, following the step of threading the catheter over a first guide wire;

FIG. 1B illustrates the catheter following the step of threading a second guide wire through the catheter from a site proximal to the balloon(s);

FIG. 1C illustrates the catheter after the first guide wire has been withdrawn from the distal linking guide wire lumen;

FIG. 1D illustrates the catheter following the step of tracking the first branch of the assembly into a branch of the body lumen; and FIG. 1E illustrates the catheter subsequent to inflation of the balloon(s).

FIGS. 2A–2F illustrate the sequential steps of deploying the catheter and prosthesis of FIG. 2. More specifically:

FIG. 2A illustrates the catheter in vivo, following the step of threading the catheter over a first guide wire;

FIG. 2B illustrates the catheter following the step of threading a second guide wire through the catheter from a site proximal to the balloon(s);

FIG. 2C illustrates the catheter after the first guide wire has been withdrawn from the distal linking guide wire lumen;

FIG. 2D illustrates the catheter following the step of tracking the first branch of the assembly into a branch of the body lumen;

FIG. 2E illustrates the catheter subsequent to inflation of the balloon(s); and

FIG. 2F illustrates a bifurcated stent following deployment and withdrawal of the catheter.

FIG. 3 is a simplified, partial, elevational view of an alternative embodiment of a balloon catheter constructed in accordance with this invention.

FIGS. 3A–3C illustrate selected sequential steps of deployment of an alternative embodiment of the invention. More specifically:

FIG. 3A illustrates the catheter in viva with a first guide wire linking the separate portions of the distal end of the assembly;

FIG. 3B illustrates the catheter following withdrawal of the first guide wire from the linking port and advancement of the second guide wire through the open distal end of the second guide wire lumen; and FIG. 3C illustrates the catheter following the positioning of the separate portion of the catheter within the branches of the vessel.

FIG. 4 is a simplified, partial embodiment of yet another alternative embodiment of the invention.

DETAILED DESCRIPTION OF THE PREFERRED EMBODIMENTS

Figure 1:
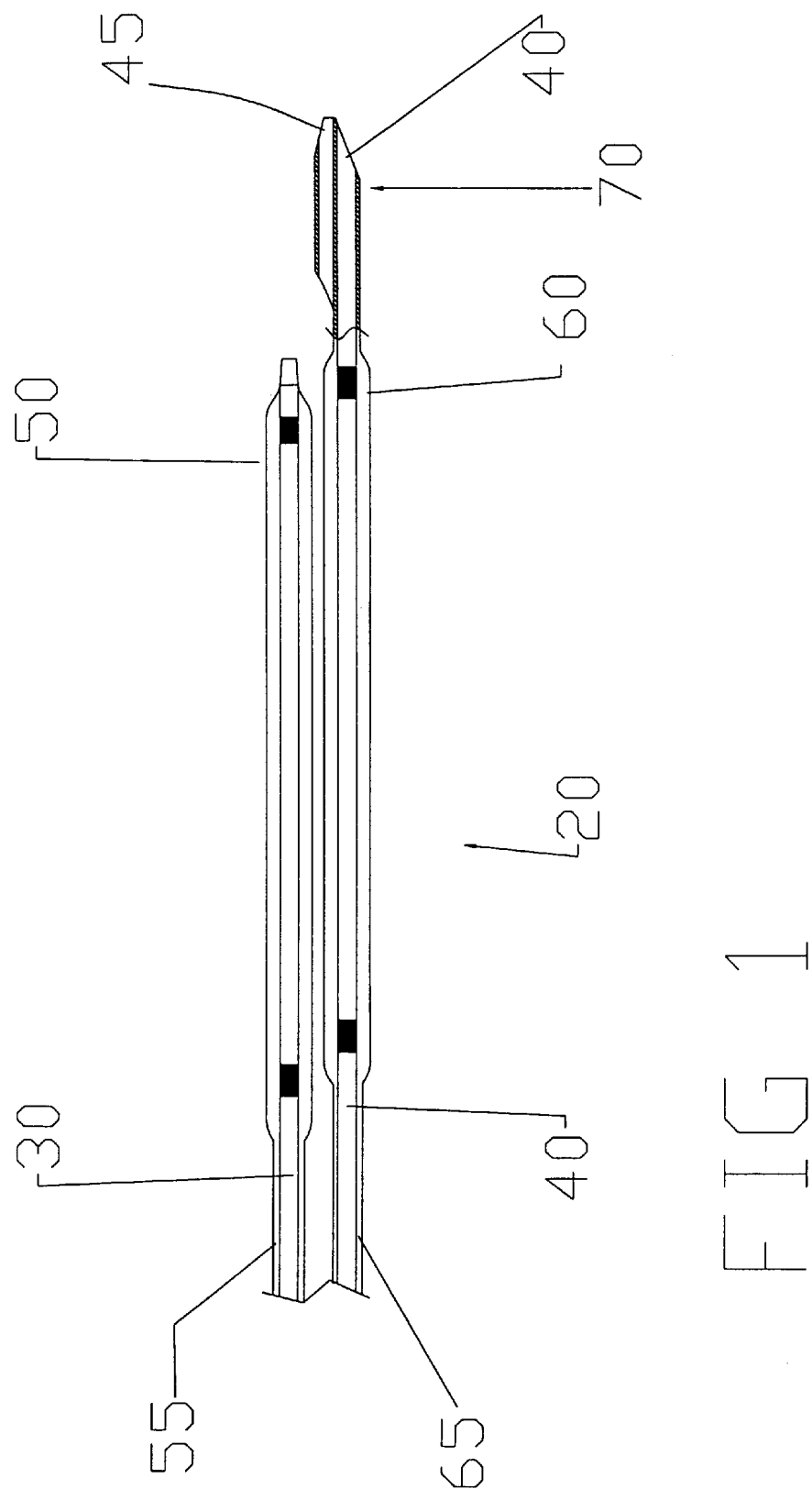
FIGS. 1 is a simplified, partial, elevational view of an illustrative embodiment of a balloon catheter constructed in accordance with this invention.
Figure 1A:
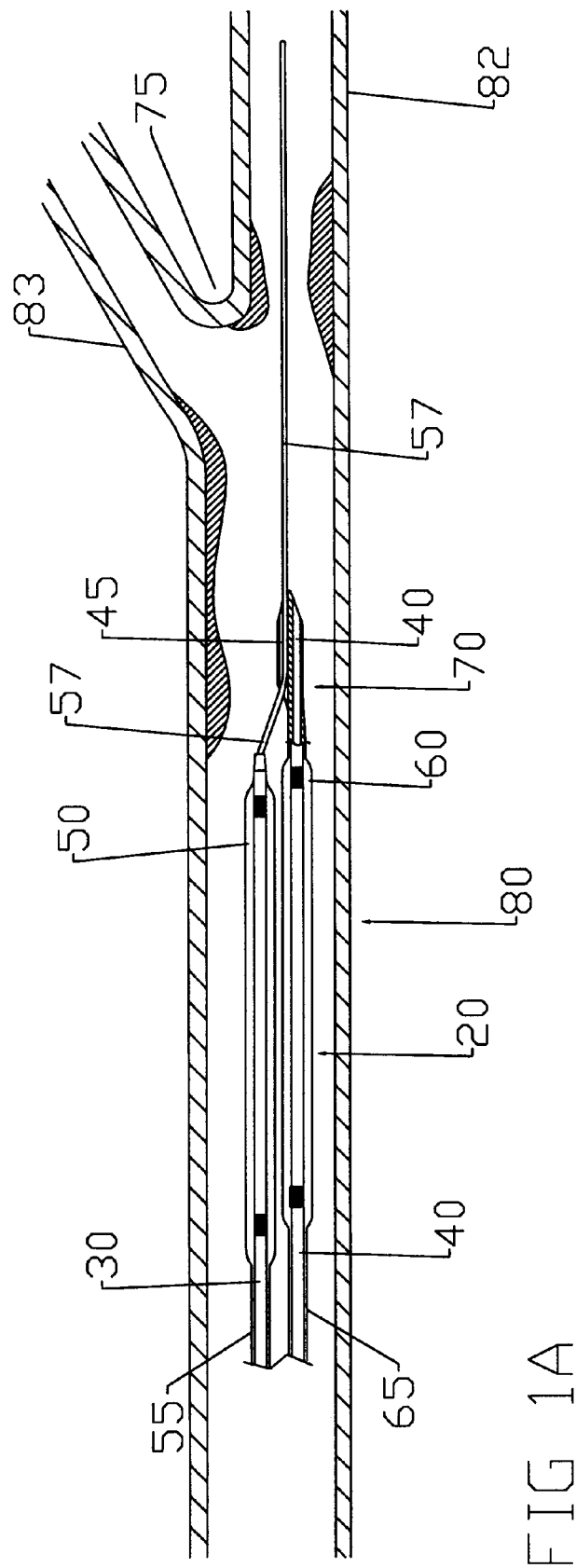
FIGS. 1A–1E illustrate the catheter of FIG. 1 following sequential steps of deployment of the catheter. More specifically.

An illustrative embodiment of a catheter 20 constructed in accordance with this invention is shown in FIG. 1. The proximal portion of catheter 20 is toward the left in FIG. 1, and the distal portion is toward the right. Catheter 20 may comprise two separate tubular structures linked at particular points along their lengths, or it may consist of a single tubular structure with multiple lumens in its interior.

FIG. 1 depicts a catheter having two balloons, but more than two balloons may be utilized with the present invention.

Alternatively, a bifurcated balloon, either alone or in combination with one or more standard balloons may be utilized.

Catheter 20 includes first balloon 50 and second balloon 60.

Inflation lumens 55 and 65 can be conventional, and extend from a portion of the catheter which always remains outside the patient which is not pictured. Inflation lumens 55 and 65 are in fluid communication with the interiors of first balloon 50 and second balloon 60. Thus inflation lumens 55 and 65 are used to supply pressurized inflation fluid to first balloon 50 and second balloon 60 when it is desired to inflate the balloons. Inflation lumens 55 and 65 are also used to drain inflation fluid from first balloon 50 and second balloon 60 when it is desired to deflate the balloons. First balloon 50 and second balloon 60 are initially deflated.

Catheter 20 also includes first guide wire lumen 30, which extends through first balloon 50, and distally therefrom. Alternatively, first guide wire lumen 30 may not pass through the interior of first balloon 50. For example, the lumen may be affixed to the exterior of the balloon, or the balloon may be formed with a plurality of folds through which the guidewire passes. Or the guidewire may pass through the folds of the balloon, as illustrated in copending application Ser. No. 08/624,692 for a Rapid Exchange Folded Balloon Catheter and Stent Delivery System. Although first guide wire lumen 30 extends through first balloon 50 in the embodiment depicted in FIGS. 1–2F, it is distinct from inflation lumen 55 and is not in fluid communication with the interior of the balloon. Further, first guide wire lumen 30 can begin and terminate generally at any point along first balloon 50, but preferably extends distally of first balloon 50.

Figure 1B:
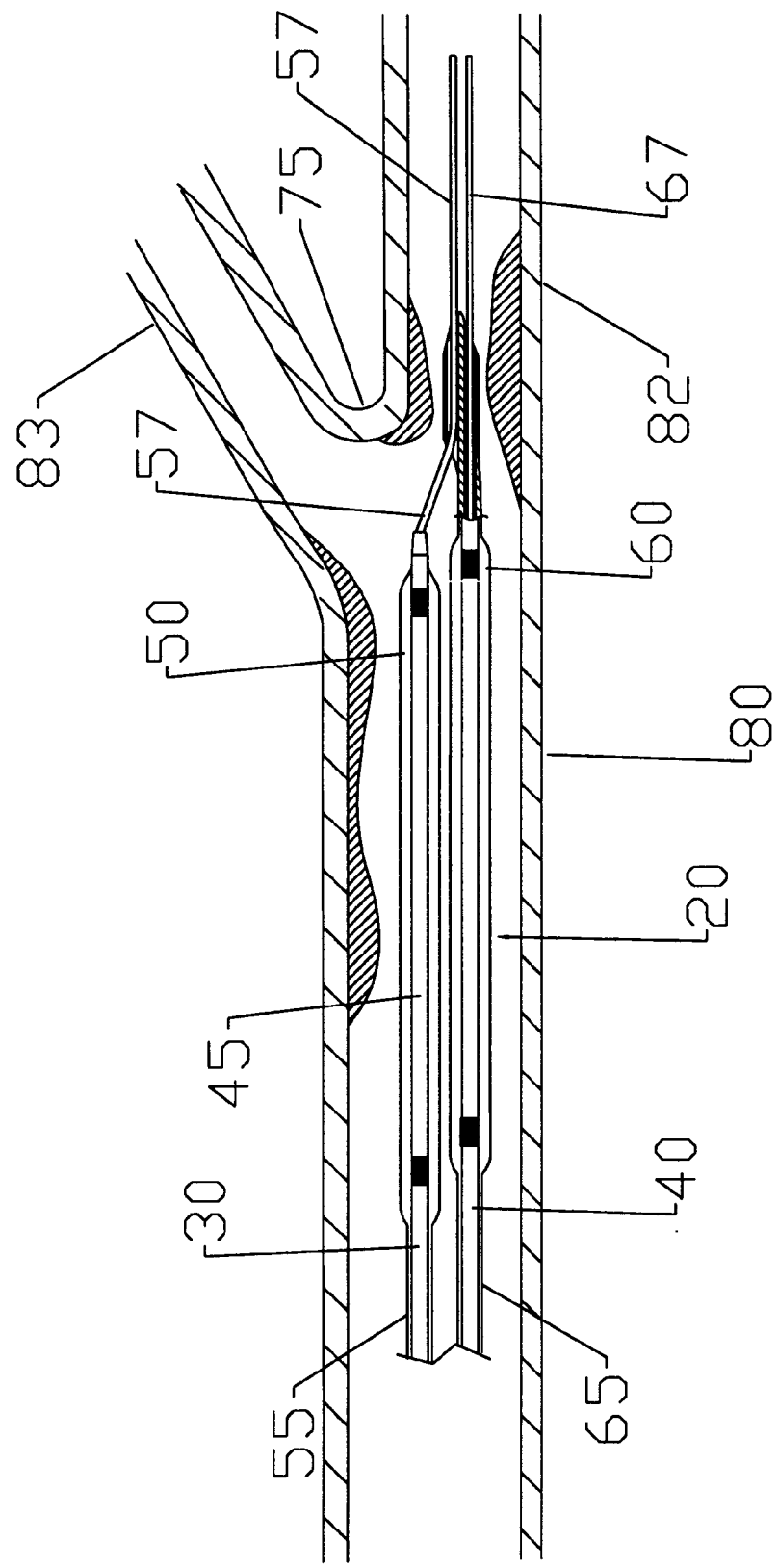
Figure 1C:
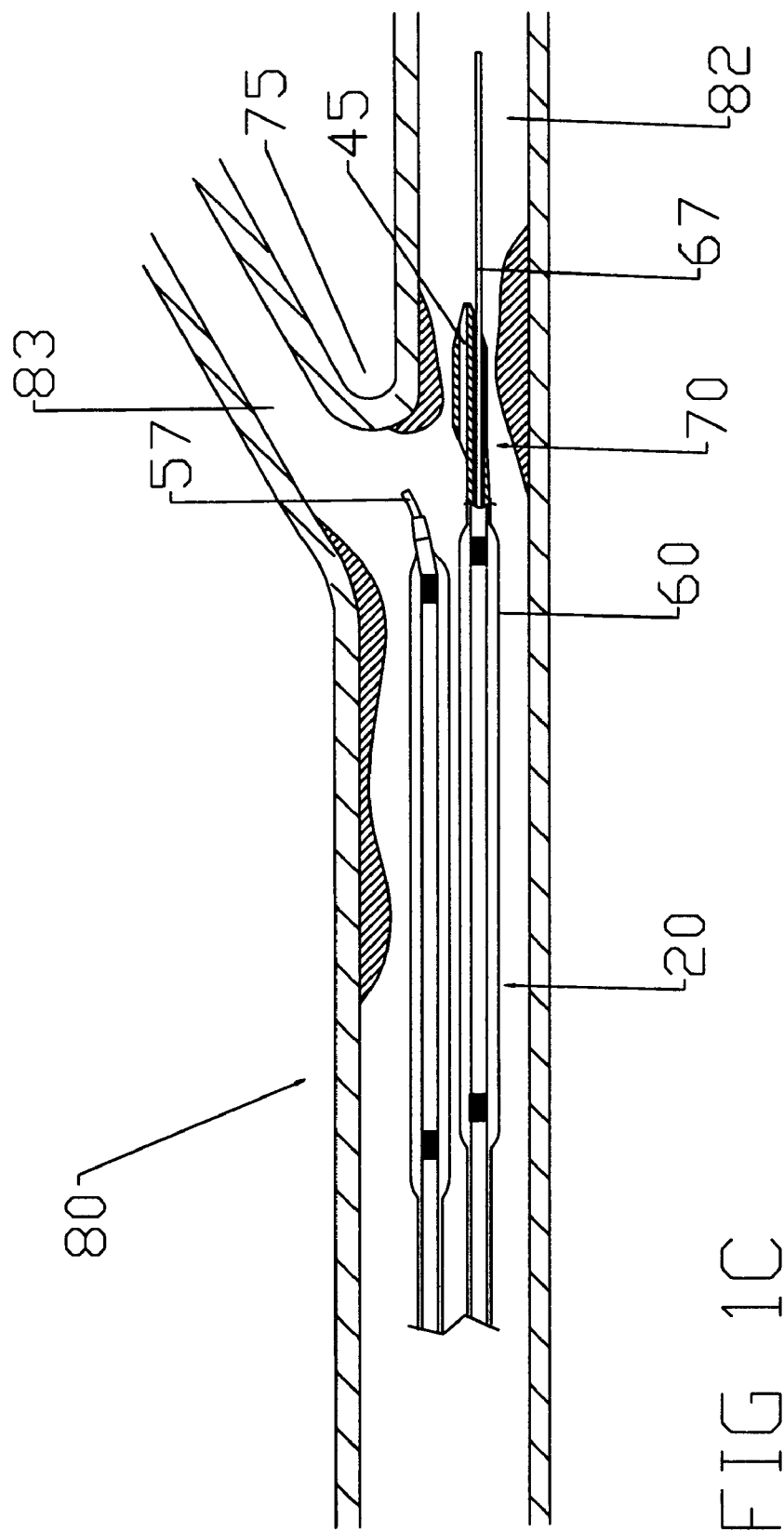
Figure 1D:
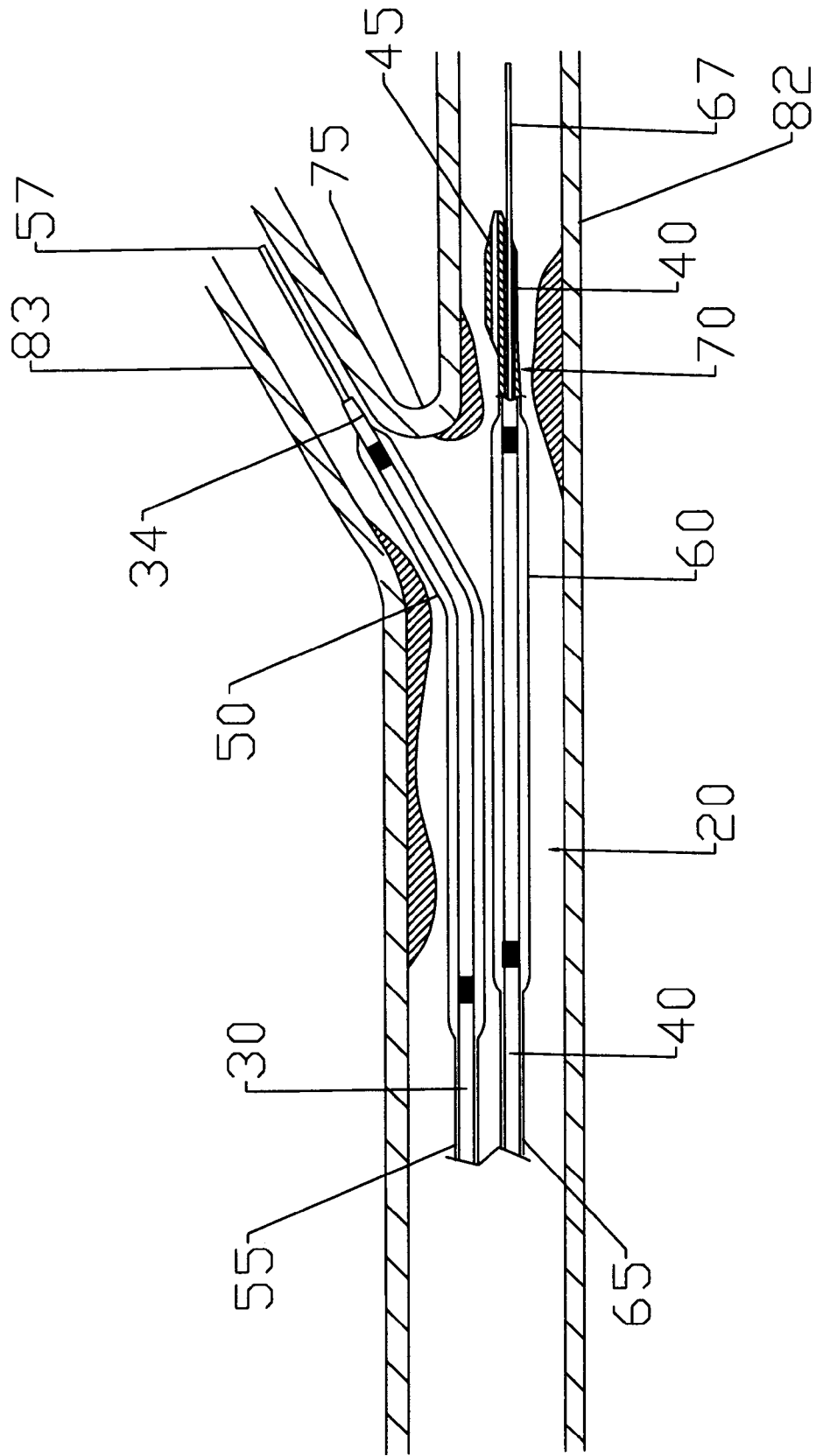
Figure 1E:
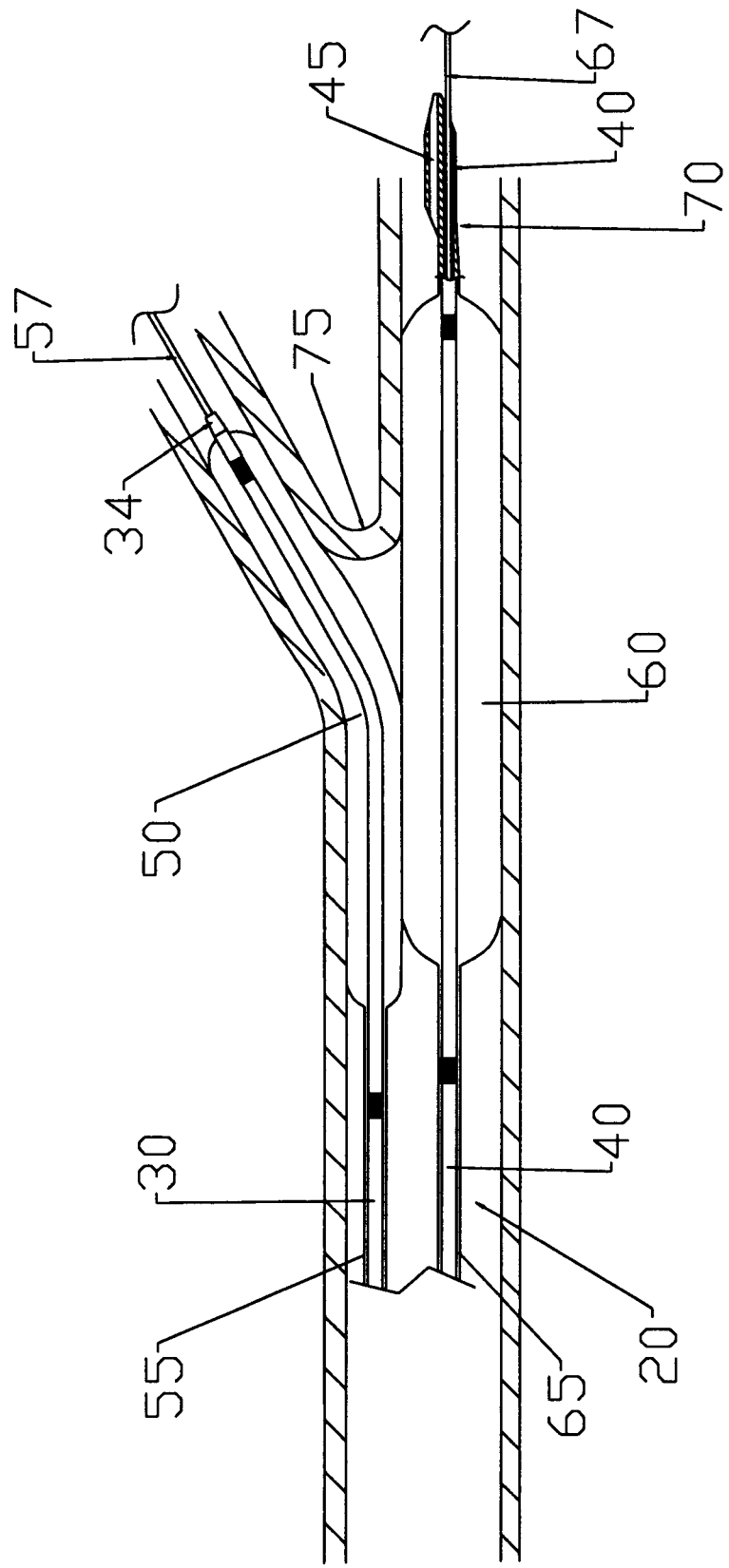

In the embodiment depicted in FIGS. 1–1E, second guide wire lumen 40 similarly extends through the interior of second balloon 60, but is distinct from inflation lumen 65 and is not in fluid communication with the interior of second balloon 60. Second guide wire lumen 40 also preferably extends distally of second balloon 60, and may comprise a proximal open end at any point along the length of the catheter.

Distal tip structure 70 houses linking guide wire lumen 45 and a portion of second guide wire lumen 40. Linking guide wire lumen 45 preferably begins and terminates distally of second balloon 60.

With reference to FIGS. 1A–E, the manner of practicing the invention will now be discussed. Catheter 20 is threaded over a first guide wire which is already in place in the body lumen. More specifically, the proximal end of first guide wire 57 is threaded into the distal open end of linking guide wire lumen 45. First guide wire 57 emerges from the proximal open end of linking guide wire lumen 45 and is then threaded into the distal open end of first guide wire lumen 30, and extends through a proximal open end thereof, at some point along the length of catheter 20.

Catheter 20 is thus threaded over first guide wire 57 and tracked to a position at or near bifurcation 75 of vessel 80, as depicted in FIG. 1B. Distal tip structure 70 is placed slightly within first branch 82 of vessel 80.

Second guide wire 67 is then threaded into catheter 20 from the proximal end of the catheter. More specifically, second guide wire 67 is threaded into the open proximal end of second guide wire lumen 40, and may extend therefrom through the open distal end of guide wire lumen 40, as depicted in FIG. 1B.

With catheter 20 positioned near bifurcation 75, and with the distal tip structure 70 positioned within a first branch 82 of the bifurcated vessel 80, first guide wire 57 is withdrawn from linking guide wire lumen 45. (See FIG. 1C). The first and second balloons can then be positioned independently of one another. Second guide wire 67 remains in second guide wire lumen 40, and distal tip structure 70, which remains in first branch 82 of vessel 80. First guide wire 57 remains within first guide wire lumen 30, and may be further advanced and positioned in second branch 83 of vessel 80. After positioning first guide wire 57 within second branch 83, the entire assembly may be further advanced and first balloon 50 will track over first guide wire 57 into second branch 83, as depicted in FIG. 1D.

Once the entire assembly is properly positioned, pressurized fluid is supplied to first and second balloons 50 and 60, as shown in FIG. 1E. After first balloon 50 and second balloon 60 have been inflated as described above, first balloon 50 and second balloon 60 are deflated by draining the inflation fluid via inflation lumens 55 and 65. This allows the balloons to collapse in preparation for withdrawal of the assembly from vessel 80.

Figure 2:
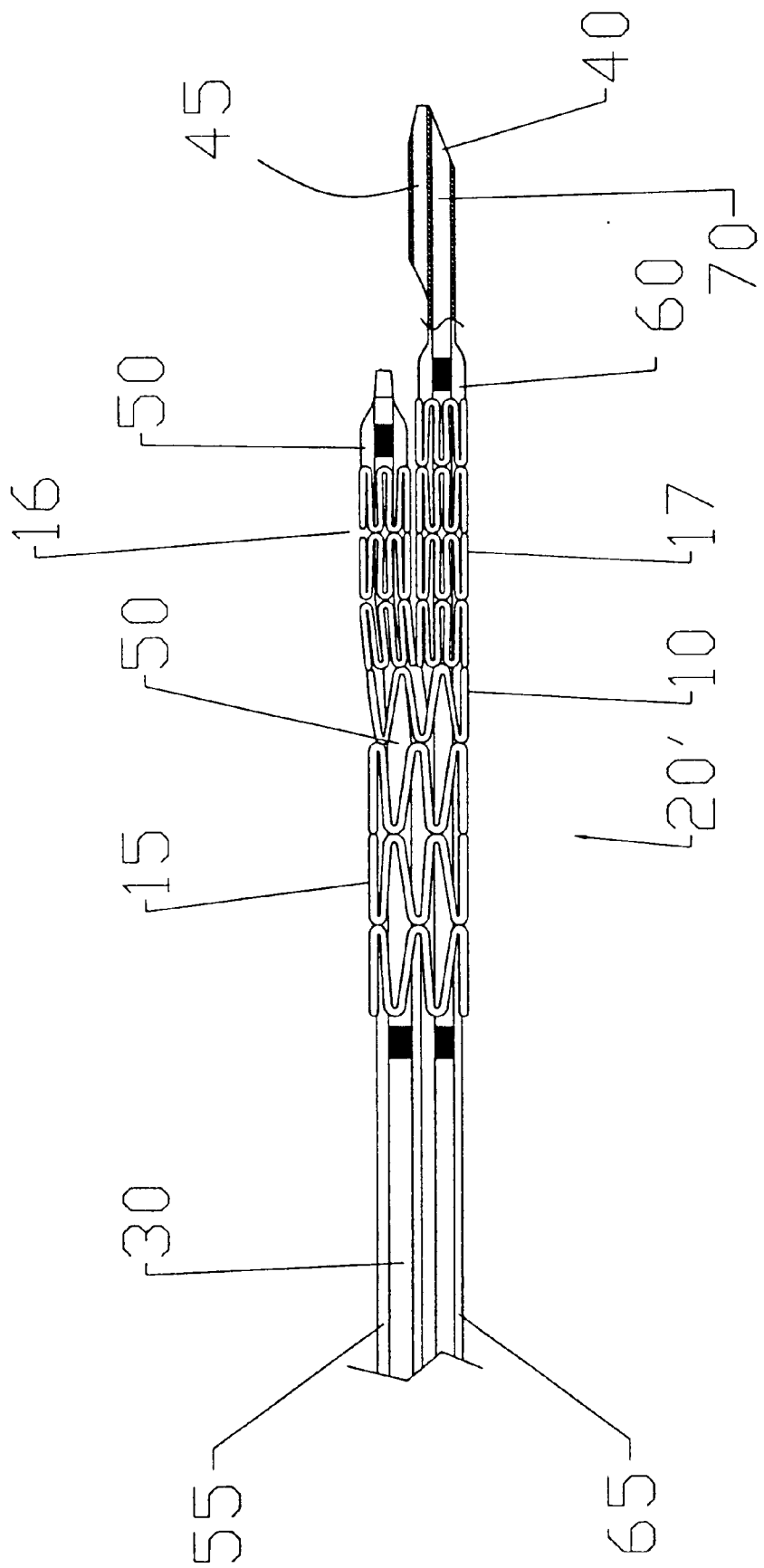
FIG. 2 is a simplified, partial, elevational view of an illustrative embodiment of a balloon catheter constructed in accordance with this invention with an endoluminal prosthesis mounted thereon.
Figure 2A:
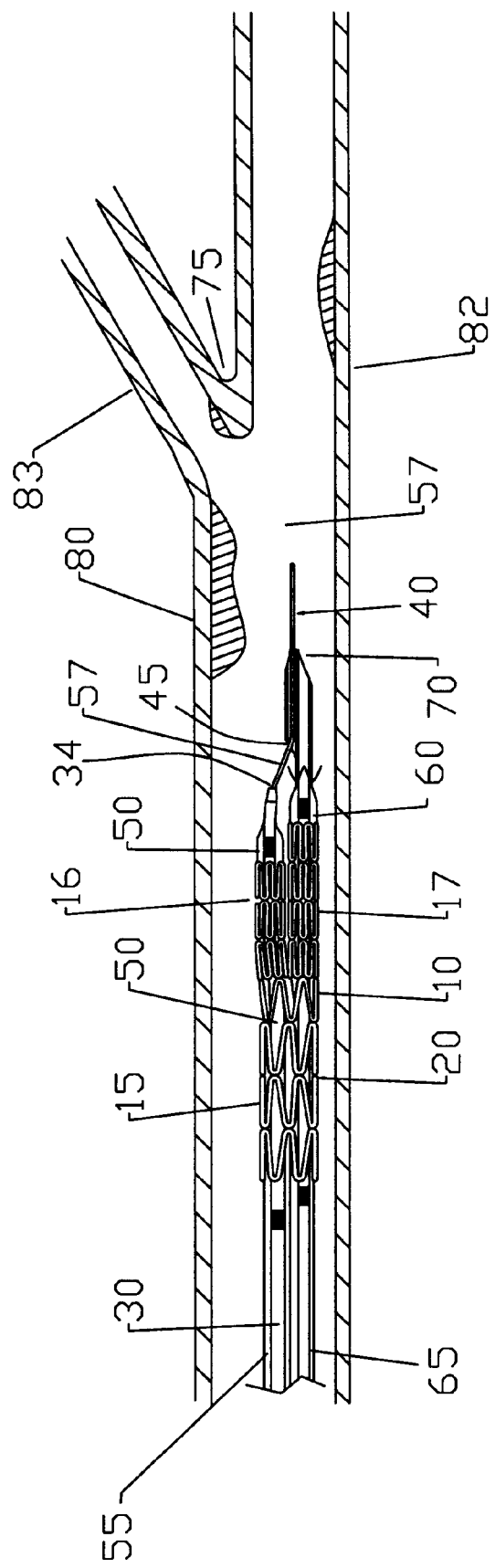
Figure 2B:
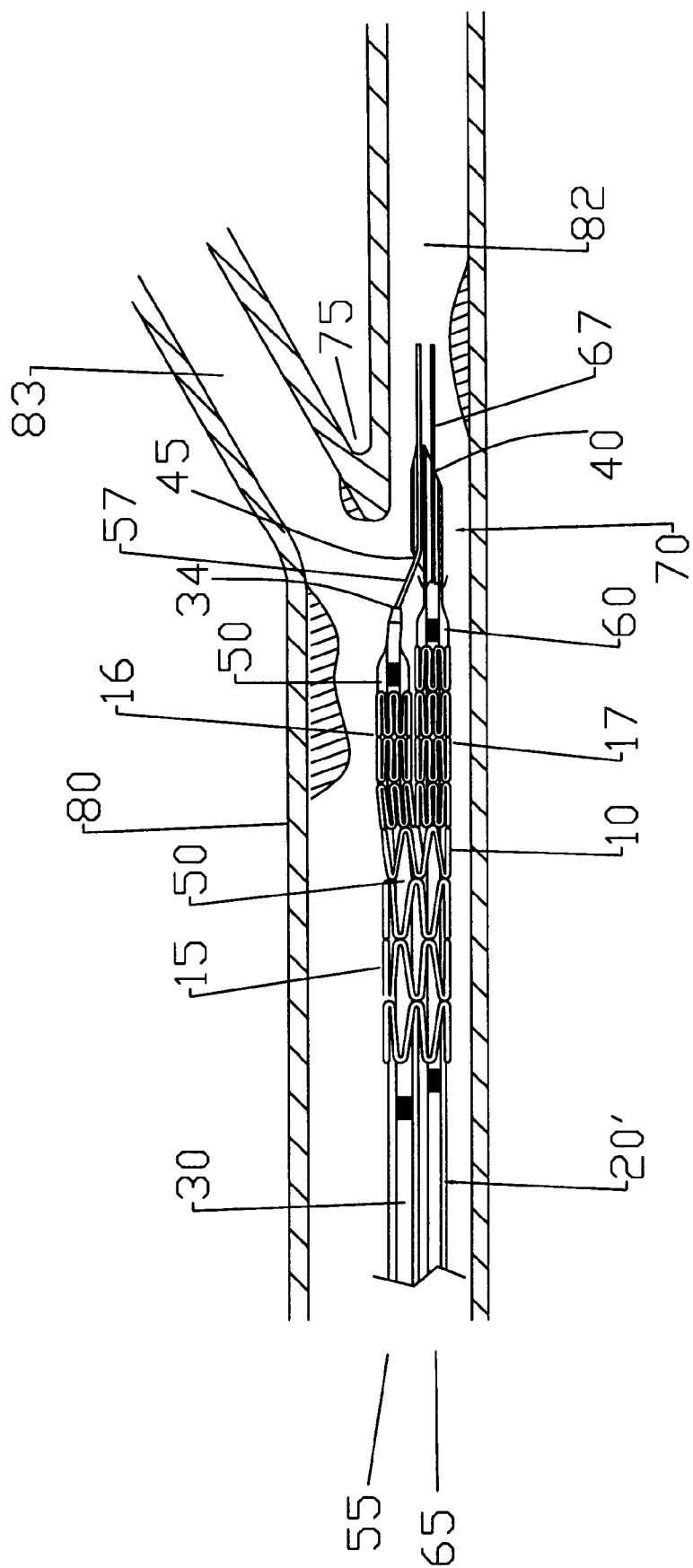
Figure 2C:
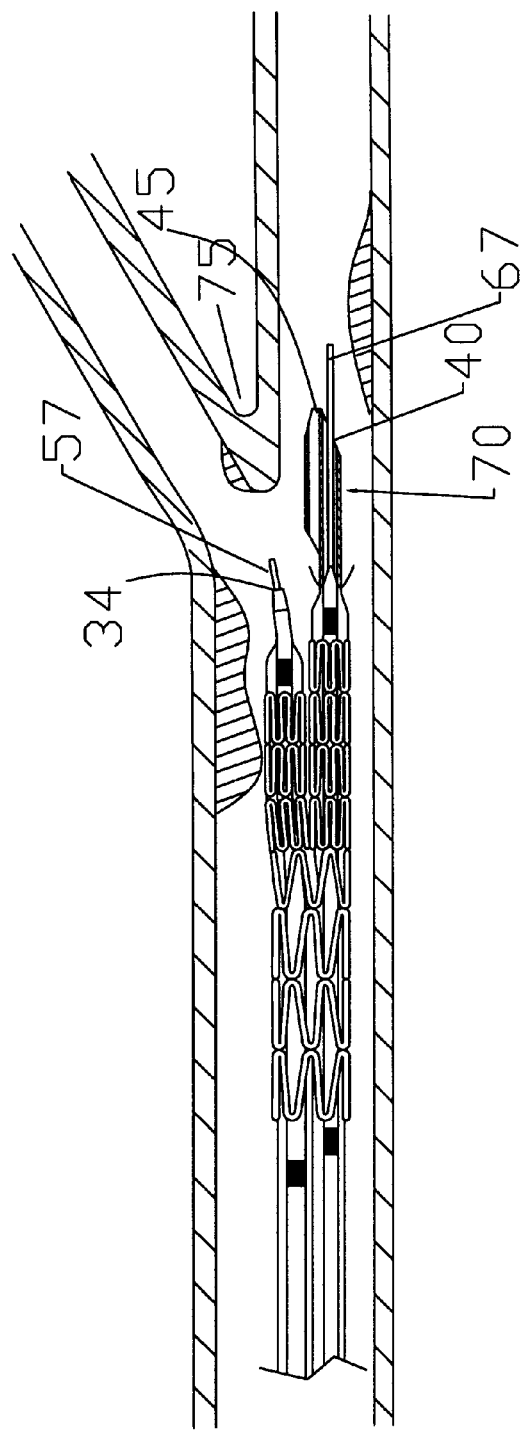
Figure 2E:
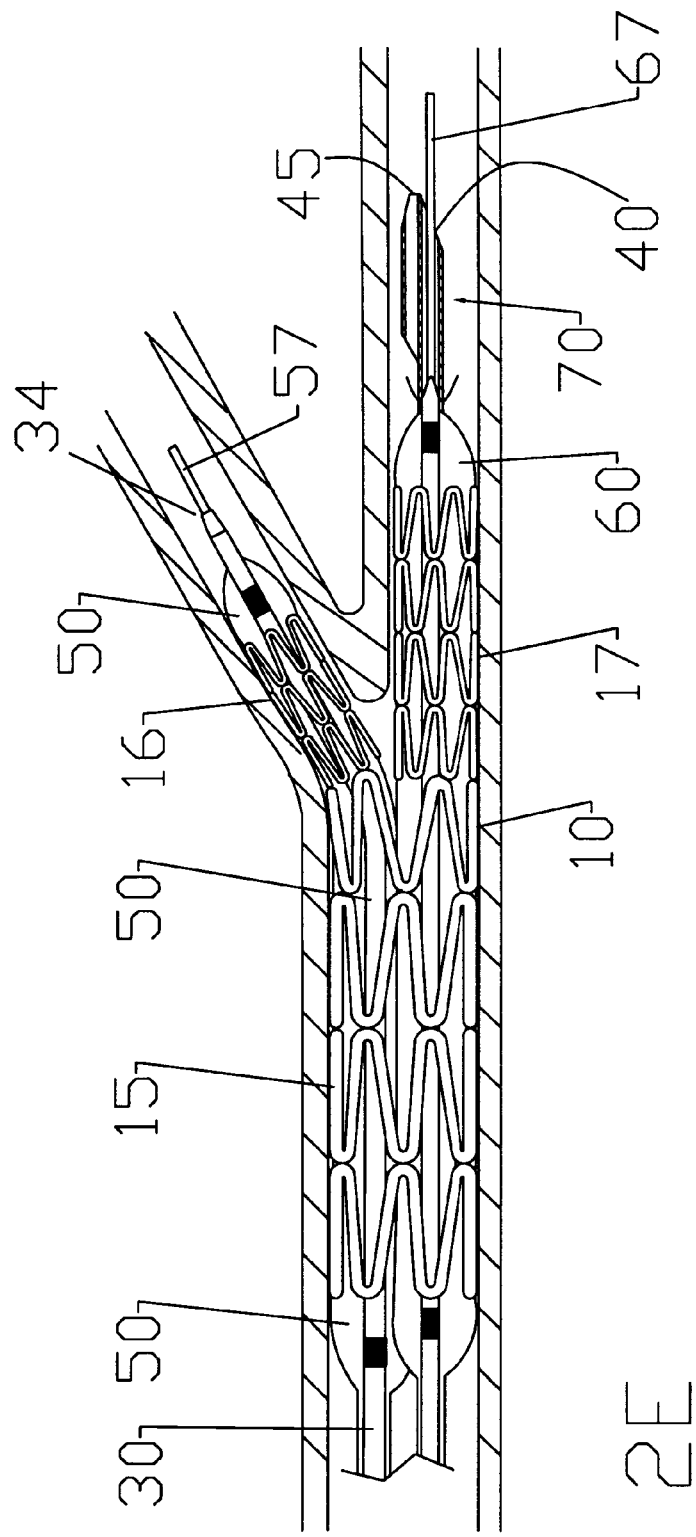

FIGS. 2–2F illustrate the foregoing embodiment with a bifurcated stent mounted upon first and second balloons 50 and 60. FIGS. 2–2F depict the use of catheter 20' for the implantation of stent 10. A single bifurcated stent 10 is depicted in FIGS. 2–2F, but multiple stents, in place of or in combination with a bifurcated stent, may be deployed utilizing the present invention. Stent structure 10, mounted upon catheter 20', comprises a trunk 15 and generally cylindrical legs 16 and 17. Stent structure 10 is mounted such that trunk 15 is annularly disposed about both first balloon 50 and second balloon 60. Leg 16 is annularly disposed only about first balloon 50. Similarly, leg 17 is disposed only about second balloon 60.

Catheter 20' is delivered and deployed in the same fashion as demonstrated in FIGS. 1A–1E. When pressurized balloon inflation fluid is supplied to first and second balloons 50 and 60, the balloons inflate and circumferentially expand stent 10. After first balloon 50 and second balloon 60 have been inflated and stent 10 thereby implanted as described above, first balloon 50 and second balloon 60 are deflated by draining the inflation fluid via inflation lumens 55 and 65. This allows the balloons to collapse in preparation for withdrawal of the assembly from vessel 80. FIG. 2F illustrates the deployed stent 10 in vessel 80 following withdrawal of catheter 20'.

Figure 3A:
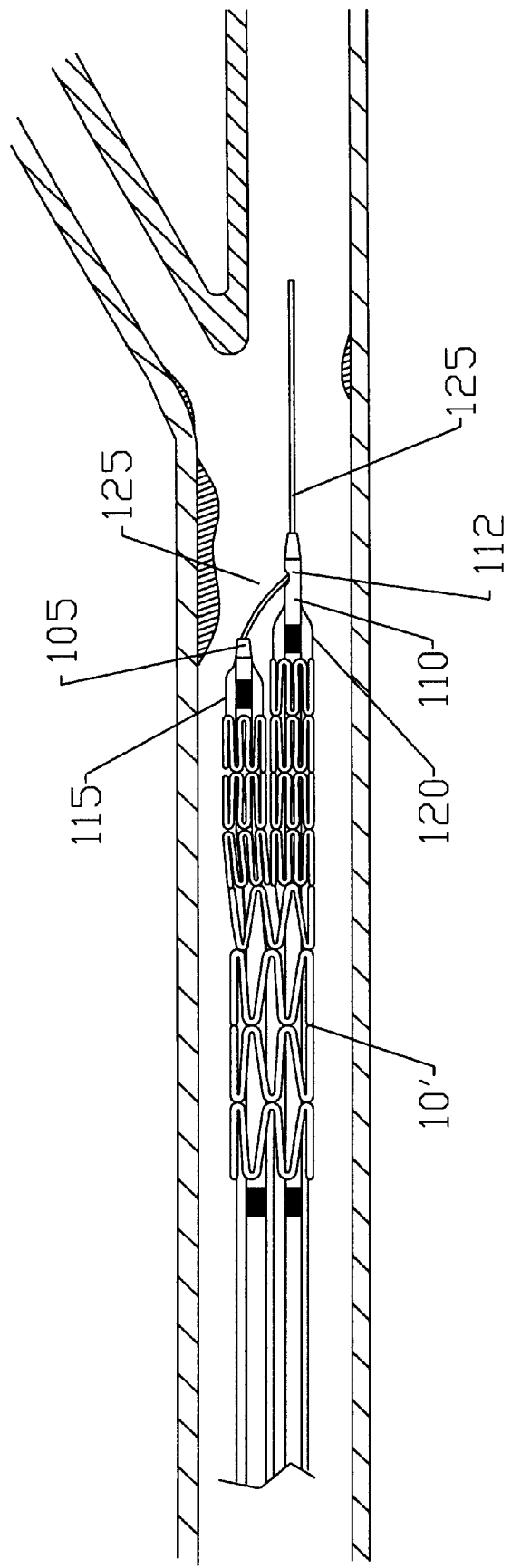

Turning now to an alternative embodiment of the invention depicted in FIG. 3, catheter 100, with stent 10' mounted thereon, comprises a first guide wire lumen 105, a second guide wire lumen 110, a first balloon 115 and second balloon 120. Second guide wire lumen 110 also comprises a side access port 112. In order to use catheter 100, a first guide wire 125, which is in place in the body, is threaded through the open distal end of second guide wire lumen 110, and out side access port 112. First guide wire 125 is then threaded into the open distal end of first guide wire lumen 105, and catheter 100 is tracked over the guide wire to the treatment site, as shown in FIG. 3A.

Figure 3B:
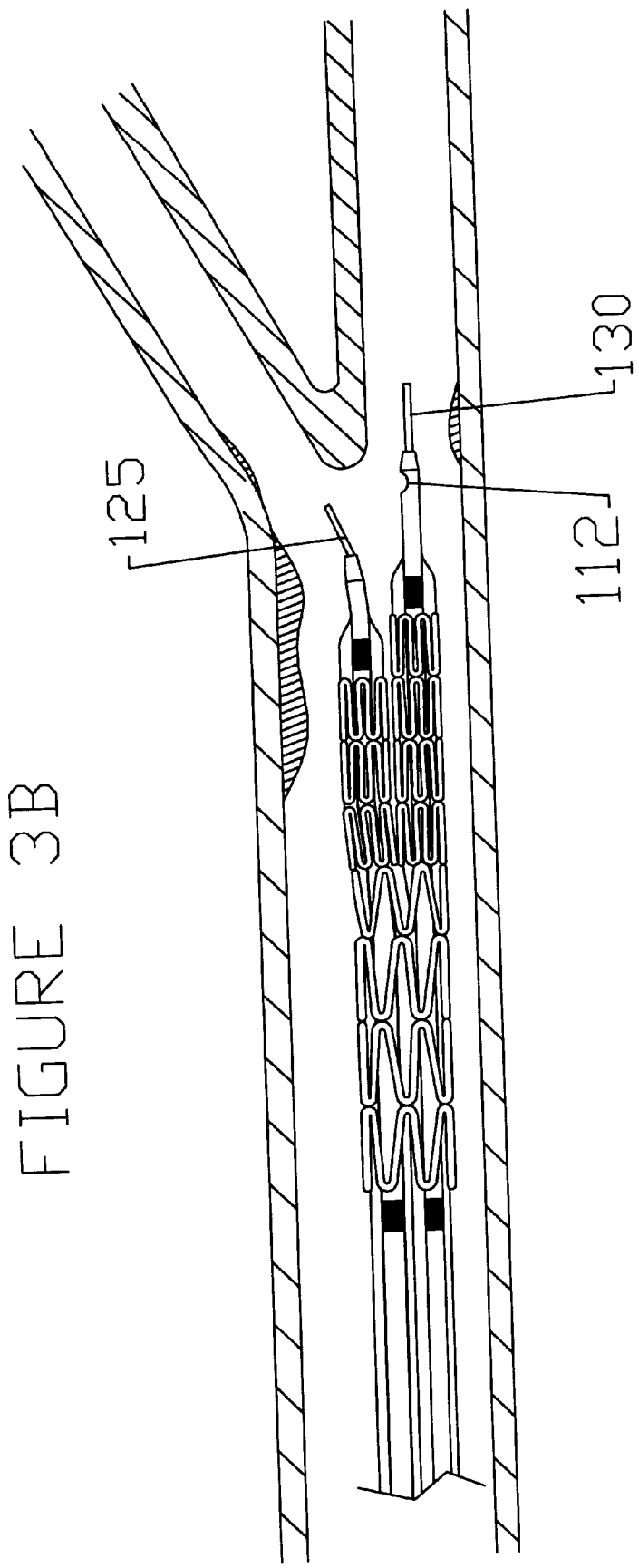

Continuing with the deployment of catheter 100, second guide wire 130 is threaded into the open proximal end of second guide wire lumen 110. Second guide wire 130 is passed through the lumen until its passage is blocked by first guide wire 125. First guide wire 125 is then retracted a short distance such that it withdraws from the side access port 112 of second guide lumen 110. Second guide wire 130 can then be advanced through the distal opening of second guide wire lumen 110, as shown in FIG. 3B. Catheter 100 can then be positioned within the branches of the body lumen, as shown in FIG. 3C, and deployed in the same fashion as the embodiment described above.

Another embodiment of the present invention is illustrated in FIG. 4, as catheter 200. Catheter 200 comprises a first guide wire lumen 205, a second guide wire lumen 210, and distal tip structure 230. Distal tip structure 230 includes a housing 215 for linking the distal ends of the catheter. First guide wire 208 is in place in the body lumen prior to the introduction of catheter 200. Second guide wire 212 is threaded into the open proximal end (not pictured) of second guide wire lumen 210, and into guide wire linking lumen 215. The proximal end of first guide wire 208 is then threaded into the distal open end of first guide wire lumen 205, and catheter 200 is tracked to the treatment site. Once appropriately positioned near the bifurcation of the vessel, second guide wire 212 is retracted until it withdraws from linking guide wire lumen 215. Catheter 200 can then be positioned within the bifurcation of the vessel, and deployed in the same fashion as the embodiments described above.

Figure 5:
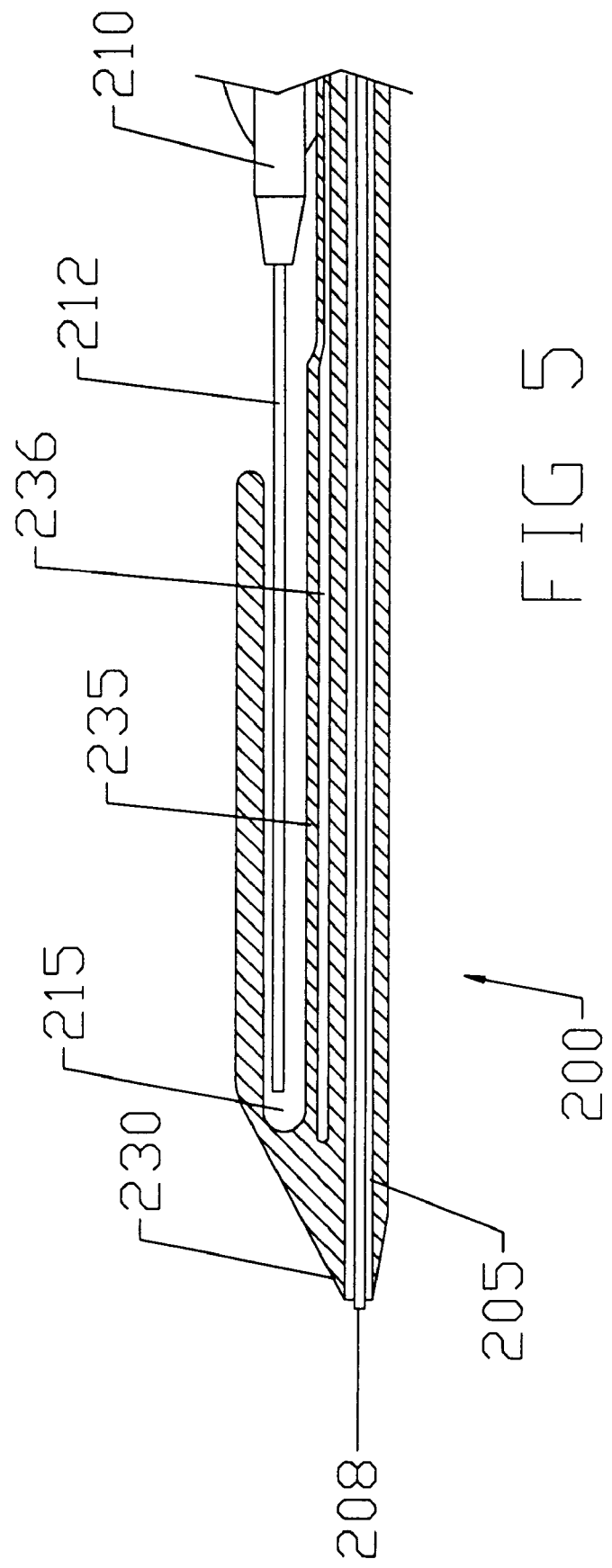
FIG. 5 illustrates the embodiment depicted in FIG. 4 with an added optional feature.

A variation of the embodiment depicted in FIG. 4 is depicted in FIG. 5. The added features depicted in FIG. 5 include a thin wall 235 lining housing 215, and an inflation lumen 236 between housing lumen 215 and first guide wire lumen 205. Pressurized inflation fluid is delivered to inflation lumen 236, and thin wall 235 exerts pressure upon housing 215, securing the position of second guide wire 212 within housing 215. This prevents any inadvertent dislodgment of second guide wire 212 while being advanced to the treatment site.

Figure 6:
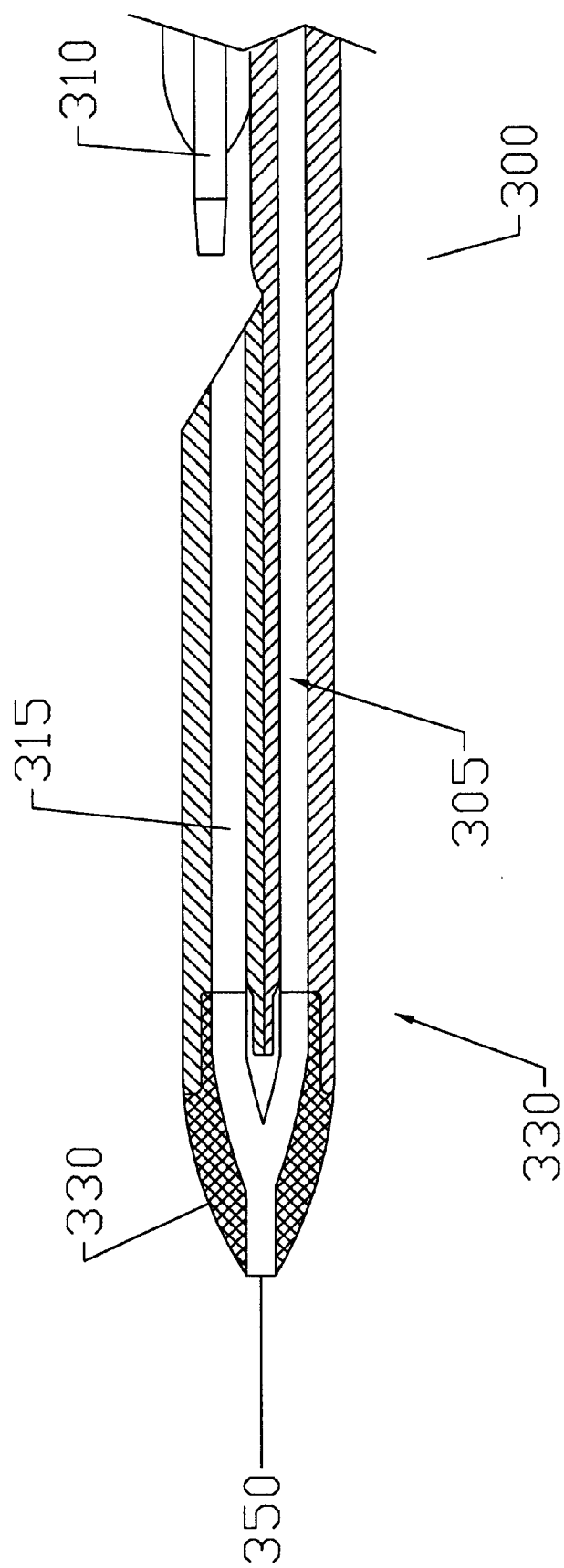
FIG. 6 is a simplified, partial embodiment of yet another embodiment of the invention.

Turning now to FIG. 6, catheter 300 represents yet another embodiment of the invention. Catheter 300 comprises first guide wire lumen 305, second guide wire lumen 310 and distal tip structure 330. Distal tip structure 330 includes a distal section of second guide wire lumen 310, linking guide wire lumen 315 and distal port 350. Catheter 300 can be tracked over either a guide wire which links the distal end of the catheter, or a guide wire which extends through second guide wire lumen 310, depending upon the choice of the user. In use, a first guide wire is in place in the body. Second guide wire (not shown) is threaded into either second guide wire lumen 310 and guide wire linking lumen 315, or into first guide wire lumen 305. The proximal end of first guide wire (not pictured), is threaded into the distal port 350, and catheter 300 is tracked to the treatment site. Once appropriately positioned near the bifurcation of the vessel, second guide wire (not pictured) is retracted until it withdraws from linking guide wire lumen 315. Catheter 300 can then be positioned within the bifurcation of the vessel, and deployed in the same fashion as the embodiments described above.

The various components of the catheters of this invention can be made of the same materials that are conventionally used for generally corresponding components of known catheters. Thus, for example, the various lumens can be made of materials such as polyethylene, polyethylene terephthalate, polyurethanes, polyesters, polyamides and copolymers thereof.

As another example, at least part of inflation lumen 55 and 65 may be stainless steel, polyimide or the like. A polyimide hyptotube or similar material may encase the proximal shaft of the catheter. A sufficiently rigid material may prevent the twisting of the catheter and potential distortion of the lumens and guide wires within the catheter in the event a torque is applied to the catheter during positioning of the device.

The material of balloon 50 may be polyethylene, polyethylene terephthalate, nylon, polyamides, latex rubber, or other polymer. Stent structure 10 can be of any conventional construction (e.g., coil-wire, tubular-slotted, or braided) and can be made of any conventional stent material (e.g., stainless steel, tantalum, titanium, or nitinol). Guide wires 57 and 67 can also be of any conventional construction and material, including solid or braided stainless steel. Hence, the term "wire" is used for these elements only as a matter of convenience, and that the material may not necessarily be wire.

The dimensions (e.g., the lengths, diameters, thicknesses, etc.) of various components of the catheters of this invention may be similar to the dimensions that are conventionally used for generally corresponding components of known catheters.

A catheter or catheters and method of use for thereof for the treatment of a stenosis at a bifurcation of a body lumen have been disclosed. Although the present invention has been described in accordance with the embodiments shown, one of ordinary skill in the art will readily recognize that there could be variations to the embodiments and those variations would be within the spirit and scope of the present invention.

The invention claimed is:

1. An apparatus for treating a bifurcated region of a body lumen, comprising:
   a catheter having a proximal end and a distal end;
   first and second expandable portions at the distal end of said catheter; and
   means distal of said first and second expandable portions for linking said first and second expandable portions to one another.

2. The apparatus according to claim 1 wherein said means for linking said first and second expandable portions comprises a linking guide wire lumen.

3. The apparatus according to claim 2 wherein the distal end of said catheter further comprises a distal tip structure, said linking guide wire lumen defined within said distal tip structure.

4. The apparatus according to claim 3 wherein said first portion comprises a first guide wire lumen and said second portion comprises a second guide wire lumen.

5. The apparatus according to claim 4 wherein said distal tip structure is connected to said second portion.

6. The apparatus according to claim 4 wherein said means for linking said first portion and said second portion comprises a side access port to said second guide wire lumen.

7. The apparatus according to claim 1 wherein the distal end of said catheter further comprises a distal tip structure, and said means for linking said first and second portions comprises a housing within said distal tip structure for releasably retaining a guide wire.

8. The apparatus according to claim 7 wherein said distal tip structure further comprises a distal portion of said second guide wire lumen and an inflation lumen between said distal portion of the second guide wire lumen and said housing for releasably retaining a guide wire.

9. The apparatus according to claim 4 further comprising;
   a distal port in said distal tip structure;
   said second guide wire lumen having a distal portion, and said distal portion being disposed in said distal tip structure;
   wherein said linking guide wire lumen and the distal portion of said second guide wire lumen co-terminate in the distal port.

10. A system for treating a bifurcated region of a body lumen, said system comprising:

first and second catheters, said first and second catheters each having a proximal end and a distal end;

said first catheter having a first expandable portion at the distal end thereof;

said second catheter having a second expandable portion at the distal end thereof; and means distal of said first and second expandable portions for linking the distal ends of said first and second catheters to one another.

11. The system according to claim 10 wherein said means for linking said first and second catheters comprises a linking guide wire lumen.

12. The system according to claim 11 wherein the distal end of said second catheter includes a distal tip structure, said linking guide wire lumen defined within said distal tip structure.

13. The system according to claim 12 wherein said first catheter comprises a first guide wire lumen and said second catheter comprises a second guide wire lumen.

14. The system according to claim 10 further comprising:

a distal tip disposed on the distal end of said second catheter;

said first catheter having a first guide wire lumen;

said second catheter having a second guide wire lumen; and wherein said means for linking comprises a side access port, to said second guide wire lumen, disposed on said distal tip.

15. The system according to claim 10 further comprising:

a distal tip structure disposed on the distal end of one of said first and second catheters; and said means for linking said first and second catheters comprises a housing within said distal tip structure for releasably retaining a guide wire.

16. The system according to claim 15 wherein:

said first catheter has a first guide wire lumen;

said second catheter has a second guide wire lumen;

said second guide wire lumen having a distal portion disposed in said distal tip structure; and an inflation lumen between said distal portion of said second guide wire lumen and said housing for releasably retaining a guide wire in said housing.

17. The system according to claim 13 further comprising:

a distal port in said distal tip structure;

said second guide wire lumen having a distal portion disposed in said distal tip structure;

wherein said linking guide wire lumen and the distal portion of said second guide wire lumen co-terminate in the distal port.

18. A method for treating a bifurcation region of a body lumen using a catheter system comprising a proximal and a distal end, said distal end having first and second expandable portions and a distal tip structure, the bifurcation region having at least a first and second branch, said method comprising the steps of:

accessing a body lumen;

placing a first guide wire in the body lumen and into the second branch of said bifurcation region;

threading the first guide wire through the distal tip structure;

advancing the catheter system over the first guide wire such that the distal tip structure is proximate the second branch of the bifurcation region;

positioning the first and second expandable portions of the catheter system in the first and second branches of said bifurcation region;

expanding said first and second expandable portions thereby treating the bifurcation region; and withdrawing said catheter system from the body lumen.

19. The method according to claim 18 wherein the first and second expandable portions of said catheter system include first and second guide wire lumens, respectively, and said distal tip structure includes a linking lumen and a distal section of said second guide wire lumen, and further comprising the step of:

threading the first guide wire through the linking lumen of said distal tip structure and through the first guide wire lumen prior to advancing the catheter system over the first guide wire to the bifurcation region.

20. The method according to claim 18 wherein after the step of advancing the catheter system over the first guide wire such that the distal tip structure is proximate the second branch of the bifurcation region, the method further comprises the steps of:

withdrawing the first guide wire from the second branch and the distal tip structure;

placing the first guide wire into the first branch of said bifurcation region;

advancing a second guide wire through the second guide wire lumen and distal tip structure into the second branch of said bifurcation region such that the first and second expandable portions of the catheter system can be advanced over the first and second guide wires.

21. The method according to claim 18 wherein at least one of said first and second expandable portions further comprises at least one mounted endoluminal prosthesis, and said at least one endoluminal prosthesis is implanted in the body lumen upon expansion of at least one of said expandable portions.

22. A method for treating a bifurcation region of a body lumen using a catheter system comprising a proximal and a distal end, said distal end having first and second expandable portions and a distal tip structure, said first and second expandable portions comprising first and second guide wire lumens, respectively, said distal tip structure comprising a distal portion of the second guide wire lumen and a housing for releasably retaining a guide wire, the bifurcation region having at least a first and second branch, said method comprising the steps of:

accessing a body lumen;

placing a first guide wire in the body lumen and into the second branch of said bifurcation region;

threading a second guide wire through the second guide wire lumen and into the housing for releasably retaining the guide wire;

threading the first guide wire through the distal tip structure;

advancing the catheter system over the first guide wire such that the distal tip structure is proximate the second branch of the bifurcation region;

withdrawing the second guide wire from the housing;

positioning the first and second expandable portions of the catheter system in the first and second branches of said bifurcation region;

expanding said first and second expandable portions thereby treating the bifurcation region; and withdrawing said catheter system from the body lumen.

23. The method according to claim 22 wherein the distal tip structure further comprises an inflation lumen between said distal portion of the second guide wire lumen and said housing for releasably retaining a guide wire, further comprising the steps of:

inflating the inflation lumen prior to tracking the catheter system over the first guide wire; and after the catheter system is advanced over the first guide wire, such that the distal tip structure is proximate the second branch of the bifurcation region, deflating the inflation lumen prior to withdrawing the second guide wire from the housing.

24. The method according to claim 22 wherein at least one of said first and second expandable portions further comprises at least one mounted endoluminal prosthesis, and said at least one endoluminal prosthesis is implanted in the body lumen upon expanding said first and second expandable portions.

* * * * *